(12) United States Patent
Yoshida et al.

(10) Patent No.: US 7,806,169 B2
(45) Date of Patent: Oct. 5, 2010

(54) HEAT EXCHANGER, METHOD FOR MANUFACTURING THE SAME, AND HEART-LUNG MACHINE

(75) Inventors: Shinichi Yoshida, Hiroshima (JP); Minoru Tanaka, Hiroshima (JP); Tomokazu Niitsuma, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 1138 days.

(21) Appl. No.: 10/584,478

(22) PCT Filed: Feb. 7, 2005

(86) PCT No.: PCT/JP2005/001757

§ 371 (c)(1),
(2), (4) Date: Jun. 23, 2006

(87) PCT Pub. No.: WO2005/075922

PCT Pub. Date: Aug. 18, 2005

(65) Prior Publication Data

US 2009/0018629 A1    Jan. 15, 2009

(51) Int. Cl.
*F28F 9/02* (2006.01)

(52) U.S. Cl. .................. 165/158; 165/175; 165/140

(58) Field of Classification Search .................. 165/157, 165/158, 175, DIG. 8, 140
See application file for complete search history.

(56) References Cited

U.S. PATENT DOCUMENTS

| | | | |
|---|---|---|---|
| 3,422,884 A | * | 1/1969 | Otten ........................ 165/67 |
| 4,030,540 A | | 6/1977 | Roma |
| 4,480,683 A | | 11/1984 | Wollbeck et al. |
| 4,972,902 A | | 11/1990 | Ninomiya |

FOREIGN PATENT DOCUMENTS

| | | |
|---|---|---|
| JP | 49-17548 | 2/1974 |
| JP | 63-77053 | 5/1988 |

(Continued)

OTHER PUBLICATIONS

Affinity NT Oxygenator, Medtronic, 2000, U.S.

*Primary Examiner*—Teresa J Walberg
(74) *Attorney, Agent, or Firm*—Hamre, Schumann, Mueller & Larson, P.C.

(57) ABSTRACT

In a heat exchanger including a plurality of tubes 1 through which a first fluid passes, a housing 2 in which the tubes 1 are installed, and sealing members for sealing a second fluid that flows over surfaces of the tubes 1, the housing 2 includes an inlet 4 for introducing the second fluid therein and a first outlet 5 and second outlets 6 for discharging the second fluid, and the sealing members include a first sealing member 3*a* positioned on one of end sides of the tubes 1, a second sealing member 3*b* positioned on the other end side of the tubes 1, and a third sealing member 3*c* positioned between the first and second sealing members 3*a* and 3*b*. The third sealing member 3*c* is provided so that a gap 7 is provided between the first sealing member 3*a* and the third sealing member 3*c* while another gap 7 is provided between the second sealing member 3*b* and the third sealing member 3*c*, and that a flow path for the second fluid is formed therein. The second outlets 6 are provided so as to be connected to the gaps 7.

4 Claims, 11 Drawing Sheets

FOREIGN PATENT DOCUMENTS

| | | |
|---|---|---|
| JP | 63-77053 U | 5/1988 |
| JP | 3-236856 A | 10/1991 |
| JP | 6-86811 | 3/1994 |
| JP | 11-47269 | 2/1999 |
| JP | 2001-170169 | 6/2001 |

* cited by examiner

HEAT EXCHANGER, METHOD FOR MANUFACTURING THE SAME, AND HEART-LUNG MACHINE

TECHNICAL FIELD

The present invention relates to a heat exchanger, particularly to a heat exchanger used in medical equipment such as a heart-lung machine, a method for manufacturing the same, and a heart-lung machine in which the heat exchanger is used.

BACKGROUND ART

In heart surgery that involves cardiac arrest in a patient, a heart-lung machine is used for taking over the functions of respiration and circulation during the cardiac arrest. Further, during the surgery, it is necessary to lower the patient's temperature and maintain the same so that the patient's oxygen consumption should decrease. For this purpose, the heart-lung machine is equipped with a heat exchanger to control the temperature of blood taken out of the patient.

As such a medical-use heat exchanger, a bellows-type heat exchanger (see Non-Patent Document 1, for instance), a multi-tubular heat exchanger (see Patent Document 1, for instance), etc., have been known conventionally. Among these, the multi-tubular heat exchanger has a larger area used for heat exchange as compared with the bellows-type heat exchanger with the same device capacity, and hence, it has the advantage of a higher heat exchange ratio as compared with the bellows-type heat exchanger. Accordingly, the use of the multi-tubular heat exchanger is considered to contribute to the downsizing of the heart-lung machine.

Here, the conventional multi-tubular heat exchanger is described specifically with reference to FIGS. 10A, 10B, and 11. FIGS. 10A and 10B show a conventional multi-tubular heat exchanger. FIG. 10A is a top view of the same, while FIG. 10B is a front view of the same. FIG. 11 is a perspective view illustrating tubes and sealing members composing the conventional multi-tubular heat exchanger shown in FIGS. 10A and 10B. The heat exchanger shown in FIGS. 10A and 10B is a heat exchanger for medical use.

As shown in FIGS. 10A, 10B, and 11, the conventional multi-tubular heat exchanger includes a plurality of tubes 31 through which blood taken out of a patient flows, a housing 32 for housing the tubes 31, and sealing members 33a and 33b. The sealing members 33a and 33b are disposed at ends of the tubes 31 on opposite sides, respectively, so as to seal cold/hot water (heat medium) flowing over surfaces of the tubes 31. Besides, the tubes 31 are fixed in the housing 32 by the sealing members 33a and 33b. The tubes 31 are arrayed regularly at uniform pitches as shown in FIGS. 10A, 10B, and 11 to improve the heat exchange ratio. It should be noted that arrows in FIG. 10A indicate a direction of blood flow, and arrows in FIG. 10B indicate a direction of flow of cold/hot water.

A space between the sealing members 33a and 33b in the housing 32 constitutes a flow path through which cold/hot water flows. Besides, the sealing members 33a and 33b are formed in a manner such that they are in close contact with internal faces of the housing 32 and external faces of the tubes 31, whereby the sealing of cold/hot water flowing the flow path is achieved. The housing 32 is provided with an inlet 34 and an outlet 35 for cold/hot water whose positions are matched to positions of mouths of the flow path for cold/hot water.

Thus, in the heat exchanger shown in FIGS. 10A, 10B, and 11, when blood flows in through the tubes 31 while cold/hot water flows in through the inlet 34, heat exchange occurs between blood and cold/hot water via tube walls of the tubes 31, whereby the temperature of blood is adjusted. Besides, mouths of the tubes 31 on the blood outlet side are connected to an artificial lung (not shown), and blood thus subjected to temperature adjustment is fed to the artificial lung. In the artificial lung, addition of oxygen and discharge of carbon dioxide are carried out on the blood.

The heat exchanger shown in FIGS. 10A, 10B, and 11 is formed with the following procedure. First, a plate (not shown) provided with a plurality of through holes is prepared, and tubes 31 are inserted into the through holes (not shown) of the plate, respectively. Then, the tubes 31 in this state are housed in a housing 32, and the first potting is performed. Further, in a state in which the plate is removed, the second potting is performed, whereby the sealing members 33a and 33b are completed. Thus, the multi-tubular heat exchanger as shown in FIGS. 10A, 10B, and 11 is obtained.

Patent document 1: JP 11 (1999)-47269 A (FIGS. 4 and 10)
Non-patent document 1: "TRILIUM AFFINITY NT Oxygenator" Medtronic, 2000, U.S.

DISCLOSURE OF INVENTION

Problem to be Solved by the Invention

However, the multi-tubular heat exchanger as shown in FIGS. 10A, 10B, and 11 has an advantage of a higher heat exchange ratio as compared with that of the bellows-type heat exchanger, whereas it has a problem of a higher production cost as compared with the cost of the bellows-type heat exchanger since the manufacture of the same requires many steps to achieve regular arrangement of the tubes 31 at uniform pitches as described above. Such a higher cost of the heat exchanger increases the cost of the heart-lung machine, thereby resulting in an increase in expenses for medical care, i.e., an increase in the burden on a patient.

Further, in the multi-tubular heat exchanger as shown in FIGS. 10A, 10B, and 11, the cold/hot water (heat medium) normally has a pressure higher than that of blood. Therefore, when the sealing members 33a and 33b become leaky, in some cases the cold/hot water intrudes in the inside of the tubes 31, the artificial lung (not shown) connected to mouths of the tubes 31 on the blood outgoing side, etc., thereby contaminating blood.

Accordingly, it is an object of the present invention to provide a heat exchanger capable of solving the above-described problem and preventing the fluid flowing through the inside of the tubes or the fluid flowing over surfaces of the tubes from being contaminated by sealing leakage, and to provide a method for manufacturing a heat exchanger with which a decrease in the production cost can be achieved.

Means for Solving Problem

In order to achieve the foregoing problems, a heat exchanger according to the present invention includes at least a plurality of tubes through which a first fluid passes, a housing in which the tubes are installed, and sealing members for sealing a second fluid that flows over surfaces of the tubes, and is characterized as follows: the housing includes an inlet for introducing the second fluid into the housing, as well as a first outlet and a second outlet for discharging the second fluid out of the housing; the tubes are arranged in parallel with one another in the housing; the sealing members include at least a first sealing member positioned on one of end sides of the tubes, a second sealing member positioned on the other end side of the tubes, and a third sealing member positioned between the first and second sealing members; the third sealing member is provided so that a gap is provided between the first sealing member and the third sealing member while another gap is provided between the second sealing member and the third sealing member, and that a flow path is formed therein for guiding the second fluid introduced through the inlet toward the first outlet; and the second outlet is provided in the housing so as to be connected to the gaps.

Further, in order to achieve the above-described object, a heat exchanger manufacturing method according to the present invention is a method for manufacturing a heat exchanger that includes a plurality of tubes through which a first fluid passes and a housing in a tubular shape, wherein an inlet for introducing the second fluid into the housing and an outlet for discharging the second fluid are provided in sidewalls of the housing, and the method includes at least the steps of: (a) arranging the tubes in parallel with one another at intervals in a manner such that central axes of the tubes are positioned on the same plane; (b) forming a tube group by fixing and integrating the tubes in the arrayed state with use of band-like fixing members that are extended in a direction perpendicular to the central axes of the tubes so as to encircle all the tubes, the fixing members being at least two arranged at intervals along a direction of the central axes; (c) forming a heat exchange module by preparing a plurality of the tube groups and stacking the same, wherein the fixing members of each tube group are brought into close contact, in the direction of the central axes, with the fixing members of another tube groups immediately above and below the foregoing group; (d) installing the heat exchange module in the housing in a manner such that the direction of the central axes is directed in a longitudinal axis direction of the housing, wherein exposed portions of the fixing members in each tube group on surfaces of the heat exchange module are brought into close contact with or bonded with inner surfaces of the housing; and (e) filling a resin material in a manner such that a flow path for guiding the second fluid introduced through the inlet toward the outlet is formed in a space positioned between the two fixing members of each tube group in the housing, or in a manner such that the resin material is filled in interstices around the tubes between openings of the housing and the fixing members of the tube groups.

Still further, in order to achieve the above-described object, a heart-lung machine according to the present invention is characterized by including the above-described heat exchanger according to the present invention.

EFFECTS OF THE INVENTION

With the foregoing characteristics, according to the present invention, a heat exchanger is capable of preventing the fluid flowing through the inside of the tubes or the fluid flowing over surfaces of the tubes from being contaminated by sealing leakage, and it is possible also to provide a heat exchanger manufacturing method with which a multi-tubular heat exchanger can be manufactured at a lower production cost.

BRIEF DESCRIPTION OF DRAWINGS

FIG. 1A is a top view thereof, FIG. 1B is a side view thereof, and FIG. 1C is a front view thereof.

FIG. 3A is a top view thereof, FIG. 3B is a front view thereof, and FIG. 3C is a perspective view thereof.

FIG. 4A is a top view thereof, FIG. 4B is a front view thereof, and FIG. 4C is a perspective view thereof.

FIG. 6A is a top view thereof, FIG. 6B is a front view thereof, and FIG. 6C is a perspective view thereof.

FIG. 10A is a top view thereof, and FIG. 10B is a front view thereof.

DESCRIPTION OF THE INVENTION

Figure 1A:
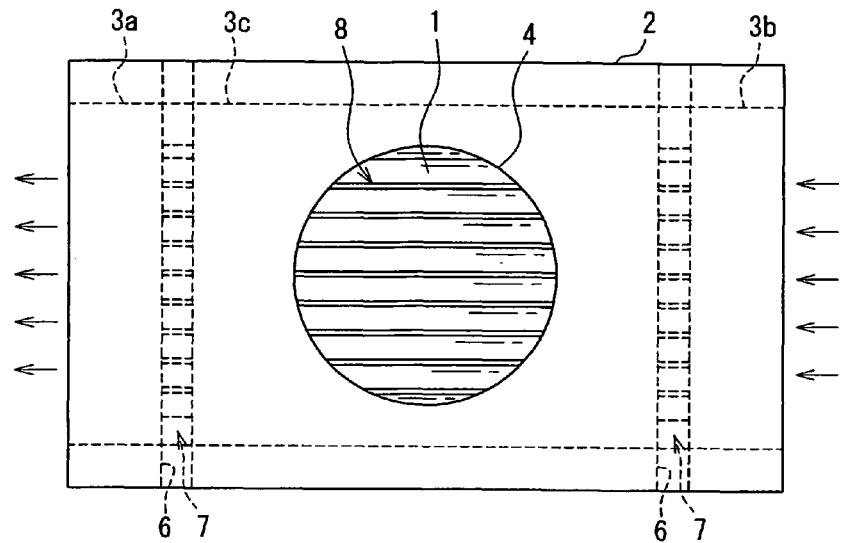
FIGS. 1A to 1C show a configuration of an example of a heat exchanger according to the present invention.

As described above, a heat exchanger according to the present invention includes at least a plurality of tubes through which a first fluid passes, a housing in which the tubes are installed, and sealing members for sealing a second fluid that flows over surfaces of the tubes, and is characterized as follows: the housing includes an inlet for introducing the second fluid into the housing, as well as a first outlet and a second outlet for discharging the second fluid out of the housing; the tubes are arranged in parallel with one another in the housing; the sealing members include at least a first sealing member positioned on one of end sides of the tubes, a second sealing member positioned on the other end side of the tubes, and a third sealing member positioned between the first and second sealing members; the third sealing member is provided so that a gap is provided between the first sealing member and the third sealing member while another gap is provided between the second sealing member and the third sealing member, and that a flow path is formed therein for guiding the second fluid introduced through the inlet toward the first outlet; and the second outlet is provided in the housing so as to be connected to the gaps. Further, a heart-lung machine according to the present invention is characterized by including therein the above-described heat exchanger according to the present invention.

The heat exchanger according to the present invention preferably is embodied so that the flow path for the second fluid is formed in a columnar shape, the inlet and the first outlet are formed in a round shape, and mouths of the flow path for the second fluid are matched with the inlet and the first outlet, respectively.

The heat exchanger according to the present invention preferably is embodied so that the tubes are arranged so that in a cross-sectional plane perpendicular to a direction of central axes of the tubes, a figure bounded by lines meeting at cross-sectional centers of three neighboring tubes is an equilateral triangle.

In the heat exchanger according to the present invention, the second fluid passing through the flow path is blood, and the heat exchanger preferably is adapted to form a part of a heart-lung machine.

A heat exchanger manufacturing method according to the present invention is a method for manufacturing a heat exchanger that includes a plurality of tubes through which a first fluid passes and a housing in a tubular shape, wherein an inlet for introducing the second fluid into the housing and an outlet for discharging the second fluid are provided in sidewalls of the housing, and the method includes at least the steps of: (a) arranging the tubes in parallel with one another at intervals in a manner such that central axes of the tubes are positioned on the same plane; (b) forming a tube group by fixing and integrating the tubes in the arrayed state with use of band-like fixing members that are extended in a direction perpendicular to the central axes of the tubes so as to encircle all the tubes, the fixing members being at least two arranged at intervals along a direction of the central axes; (c) forming a heat exchange module by preparing a plurality of the tube groups and stacking the same, wherein the fixing members of each tube group are brought into close contact, in the direction of the central axes, with the fixing members of another tube groups immediately above and below the foregoing group; (d) installing the heat exchange module in the housing in a manner such that the direction of the central axes is directed in a longitudinal axis direction of the housing, wherein exposed portions of the fixing members in each tube group on surfaces of the heat exchange module are brought into close contact with or bonded with inner surfaces of the housing; and (e) filling a resin material in a manner such that a flow path for guiding the second fluid introduced through the inlet toward the outlet is formed in a space positioned between the two fixing members of each tube group in the housing, or in a manner such that the resin material is filled in interstices around the tubes between openings of the housing and the fixing members of the tube groups.

The heat exchanger manufacturing method according to the present invention preferably is embodied so that: in the step (b), the fixing members of each tube group are four in number, which are arranged at intervals along the direction of the central axes, two of the four fixing members being inner fixing members and the other two being outer fixing members disposed relatively outward with respect to the two inner fixing members, and two inner fixing members are positioned so that the inlet and the outlet are positioned between the two inner fixing members; and in the step (e), the resin material is filled into a space between the two inner fixing members of each tube group in the housing in a manner such that a flow path for guiding the second fluid introduced through the inlet toward the outlet is formed in the space, and further, the resin material is filled in interstices around the tubes between one of the openings of the housing on one side and the outer fixing member of each tube group on the same side, as well as interstices around the tubes between the other opening of the housing on the other side and the outer fixing member of each tube group on the same side.

In the foregoing embodiment, it is preferable that the inlet and the outlet are formed, each in a round shape, at positions such that they are opposed to each other, and that in the step (e), the filling of the resin material into the space between the two inner fixing members of each tube group in the housing is carried out by rotating the housing around an axis extending from the center of the inlet to the center of the outlet.

In the above-described heat exchanger manufacturing method according to the present invention, it is preferable that in the step (c), the stacking of the plurality of tube groups is carried out in a manner such that in a cross-sectional plane perpendicular to the direction of the central axes of the tubes, a figure bounded by lines meeting at the cross-sectional center of each of the tubes in each tube group and the cross-sectional centers of two tubes most adjacent to the foregoing tube in another tube group immediately above or below the foregoing tube group is an equilateral triangle.

In the above-described heat exchanger manufacturing method according to the present invention, the following is preferred: the steps (a) and (b) are carried out by using an upper die and a lower die, in each of which a plurality of first grooves where the tubes are to be disposed and a second groove orthogonally crossing the first grooves are formed; in the step (a), the arrangement of the tubes is carried out by disposing the tubes in the first grooves in either one of the upper and lower dies; and in the step (b), the integration with use of the fixing members is carried out by joining the upper and lower dies and injecting a resin material into the space formed by the second grooves in the upper and lower dies so that the fixing members are formed by injection molding.

In the above-described heat exchanger manufacturing method according to the present invention, it is preferable that the resin material used in the step (b) for forming the fixing members by injection molding is a polycarbonate resin or a vinyl chloride resin, and that the resin material used in the step (e) is a polyurethane resin or an epoxy resin.

The following describes an example of a heat exchanger and a method for manufacturing the heat exchanger according to the present invention, while referring to the drawings. It should be noted that the heat exchanger and the method for manufacturing the heat exchanger according to the present invention are not limited to the examples described below. First, an example of a configuration of the heat exchanger according to the present invention is described, with reference to FIGS. 1A to 1C and 2.

Figure 1B:
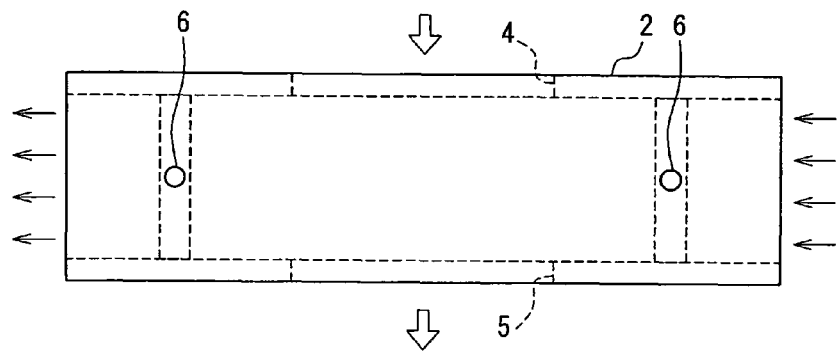
Figure 1C:
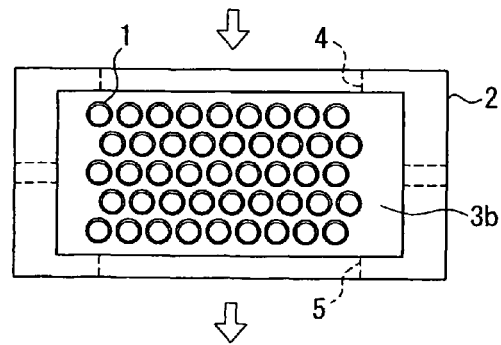
Figure 2:
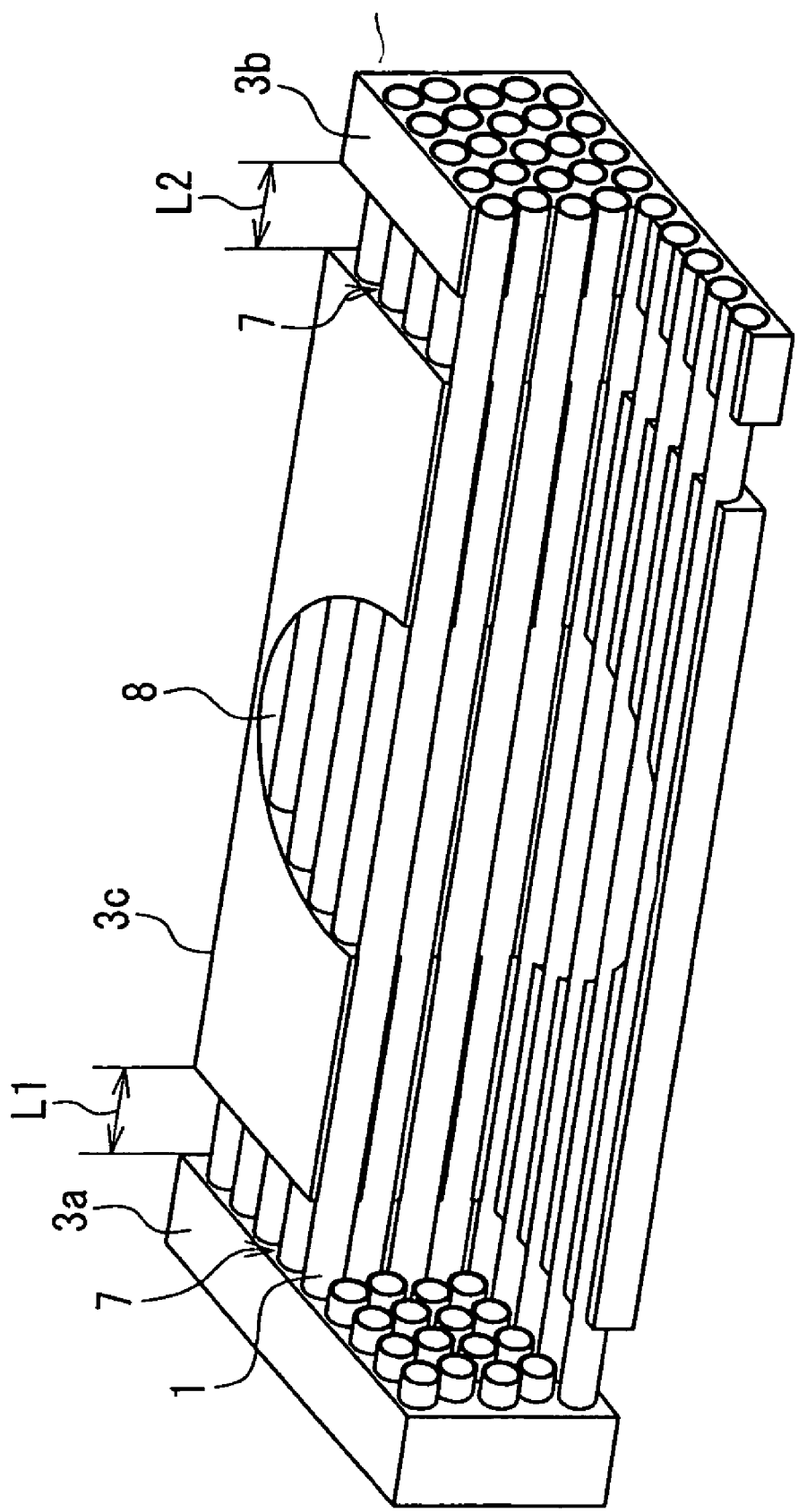
FIG. 2 is a partially cut-away perspective view showing the inside of a housing in the heat exchanger shown in FIGS. 1A to 1C.

FIGS. 1A to 1C show a configuration of an example of the heat exchanger according to the present invention. FIG. 1A is a top view thereof, FIG. 1B is a side view thereof, and FIG. 1C is a front view thereof. FIG. 2 is a partially cut-away perspective view showing the inside of a housing in the heat exchanger shown in FIGS. 1A to 1C.

As shown in FIGS. 1A to 1C, the heat exchanger according to the present embodiment includes a plurality of tubes 1 through which a first fluid flows, a housing 2 in which the tubes 1 are installed, and sealing members 3a to 3c for sealing a second fluid that flows over surfaces of the tubes 1.

As shown in FIGS. 1A to 1C and 2, the tubes 1 are arrayed in parallel with one another in the housing 2. In the example shown in FIGS. 1A to 1C and 2, the tubes 1 are arranged three-dimensionally. More specifically, the tubes 1 are arranged in the following manner such that in a cross-sectional plane perpendicular to a direction of central axes of the tubes 1 (this direction is hereinafter referred to as "tube 1 central axis direction"), a figure bounded by lines meeting at cross-sectional centers of three neighboring tubes 1 is an equilateral triangle; in other words, in a manner such that the tubes 1 in a given row are not aligned vertically with the tubes 1 in another row immediately below the foregoing given row, respectively (see FIG. 1B).

It should be noted that in the present invention, the arrangement of the tubes 1 is not limited to the example shown in FIGS. 1A to 1C and 2. For instance, the tubes 1 may be arranged so that in a cross section perpendicular to the tube 1 central axis direction, respective cross sections of the tubes 1 are arrayed in a matrix form; in other words, in a manner such that, the tubes 1 in a given row are aligned vertically with the tubes 1 another row immediately below the foregoing given row, respectively. However, with a view to improving the heat exchange ratio, the tubes 1 preferably are arranged in a manner such that the tubes 1 in a given row are not aligned vertically with the tubes 1 in the another row immediately below the foregoing given row, respectively, as shown in FIGS. 1A to 1C and 2.

The housing 2 includes an inlet 4 for introducing a second fluid into the housing, and a first outlet 5 for discharging the second fluid from the housing. The inlet 4 also constitutes an inlet of a flow path 8 for the second fluid, which will be described later, while the first outlet 5 also constitutes an outlet of the flow path 8 of the second fluid, which will be described later.

It should be noted that in the example shown in FIGS. 1A to 1C, the housing 2 is formed in a tubular shape having a rectangular cross section, and the inlet 4 and the outlet 5 are disposed respectively on sidewalls of the housing that are opposed to each other. The inlet 4 and the first outlet 5 are matched to the mouths of the flow path 8. In the present specification, "the inlet 4 and the first outlet 5 are matched to the mouths of the flow path 8" does not exclusively indicate the case where the inlet 4 and the first outlet 5 are identical to the mouths of the flow path 8. This description is meant to signify that the inlet 4 and the first outlet 5 may be continuous with the mouths of the flow path 8.

In the present invention, the cross-sectional shape of the housing 2 is not limited to the rectangular shape as shown in FIGS. 1A to 1C, but may be determined appropriately according to the arrangement of the tubes 1. The housing 2 may have any cross-sectional shape other than the rectangular shape, such as a polygonal shape, or a round shape. Further, the positions where the inlet 4 and the first outlet 5 are formed are not limited particularly. However, with a view to improving the heat exchange ratio, the inlet 4 and the first outlet 5 preferably are disposed at opposed positions in the housing 2, as shown in FIGS. 1A to 1C and 2.

Still further, as shown in FIG. 2, the sealing members include a first sealing member 3a positioned on one of end sides of the tubes 1, a second sealing member 3b positioned on the other end side of the tubes 1, and a third sealing member 3c positioned between the first and second sealing members 3a and 3b. The sealing of the tubes 1 from one another is achieved by these first, second, and third sealing members 3a, 3b, and 3c.

The third sealing member 3c is provided so as to have a gap 7 between the first sealing member 3a and itself and another gap 7 between the second sealing member 3b and itself. As seen in FIGS. 1A to 1C, the flow path 8 through which the second fluid introduced from the inlet 4 to the housing 2 is guided toward the first outlet 5 is formed by the third sealing member 3c. The third sealing member 3c functions to seal the second fluid. Still further, second outlets 6 are provided in the housing 2 so as to be continuous with the gaps 7 (see FIG. 1B).

Thus, in the heat exchanger of the present invention shown in FIGS. 1A to 1C, the sealing members positioned at ends of the tubes 1 (the first and second sealing members 3a and 3b) and the sealing member that forms the flow path 8 for the second fluid (the third sealing member 3c) are provided separately. Further, the gaps 7 are formed between the first sealing member 3a and the flow path 8 for the second fluid and between the second sealing member 3b and the flow path 8 for the second fluid.

Therefore, in the case where, for example, the second fluid leaks due to leakage of the third sealing member 3c, the second fluid having leaked is retained temporarily in the gaps 7, and thereafter is discharged through the second outlets 6 to outside the heat exchanger. In the case where the first fluid leaks due to leakage of the first sealing member 3a or the second sealing member 3b, the first fluid having leaked is retained temporarily in the gap 7, and thereafter is discharged through the second outlets 6 to outside the heat exchanger.

In other words, in the heat exchanger in the example shown in FIGS. 1A to 1C, a safety mechanism is provided to prevent the first fluid flowing through the tubes 1 from intruding into the flow path 8 and to prevent the second fluid flowing through the flow path 8 from intruding into the tubes 1. Further, by monitoring the discharge of fluid through the second outlets 6, the detection of sealing leakage can be performed. Still further, by checking discharged fluid, it can be determined which sealing member has been leaking.

Here, a case where the heat exchanger shown in FIGS. 1A to 1C is used in a heart-lung machine is considered. First, an example in which cold/hot water flows through the tubes 1 and blood flows through the flow path 8 is considered. In this example, when the first, second, and third sealing members 3a, 3b, and 3c become leaky, the cold/hot water flows toward the flow path 8 since it has a higher pressure. However, in this case, the cold/hot water having leaked out of the first or second sealing member 3a or 3b is retained in the gap 7 temporarily, and is discharged through the second outlets 6 to outside the heat exchanger. Thus, the sealing leakage can be detected, and the occurrence of blood contamination as described in the "background art" section can be prevented.

Further, in such an embodiment in which blood flows through the flow path 8, the cross-sectional shape of the flow path 8 and the shapes of the inlet 4 and the first outlet 5 preferably are round, as in the example shown in FIGS. 1A to 1C and 2. This is because by forming them in round shapes, the occurrence of thrombus can be suppressed at the flow path 8, the inlet 4, and the first outlet 5. It should be noted that in the present invention, the cross-sectional shape of the flow path 8 and the shapes of the inlet 4 and the first outlet 5 may be a rectangular shape, or another polygonal shape.

Figure 10A:
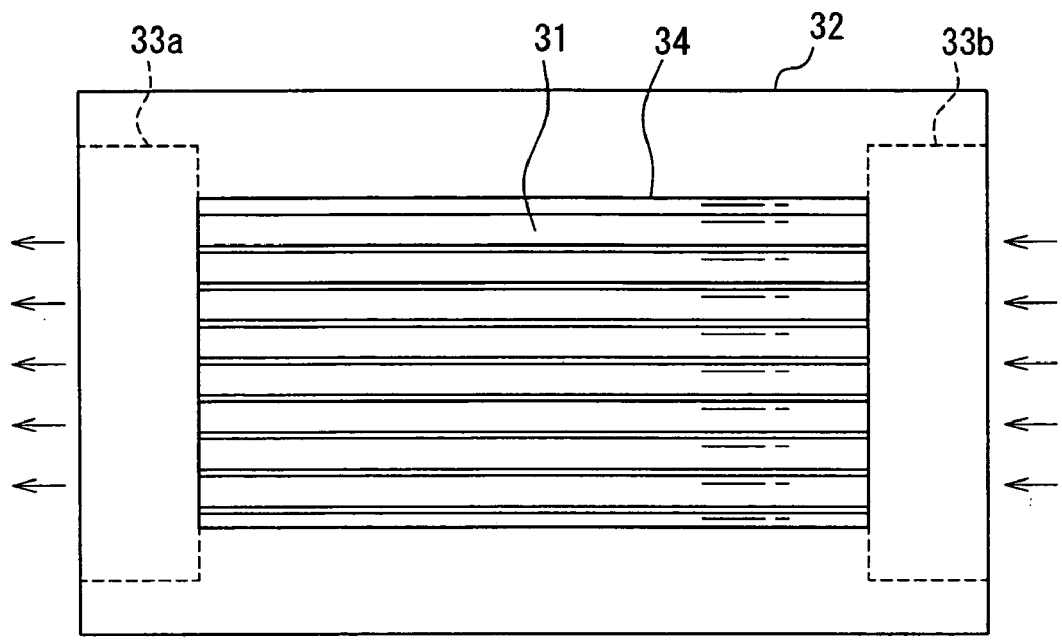
FIGS. 10A and 10B show a conventional multi-tubular heat exchanger.
Figure 10B:
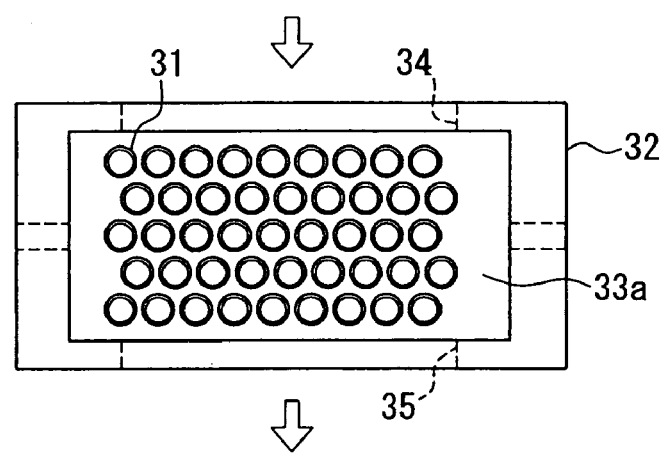
Figure 11:
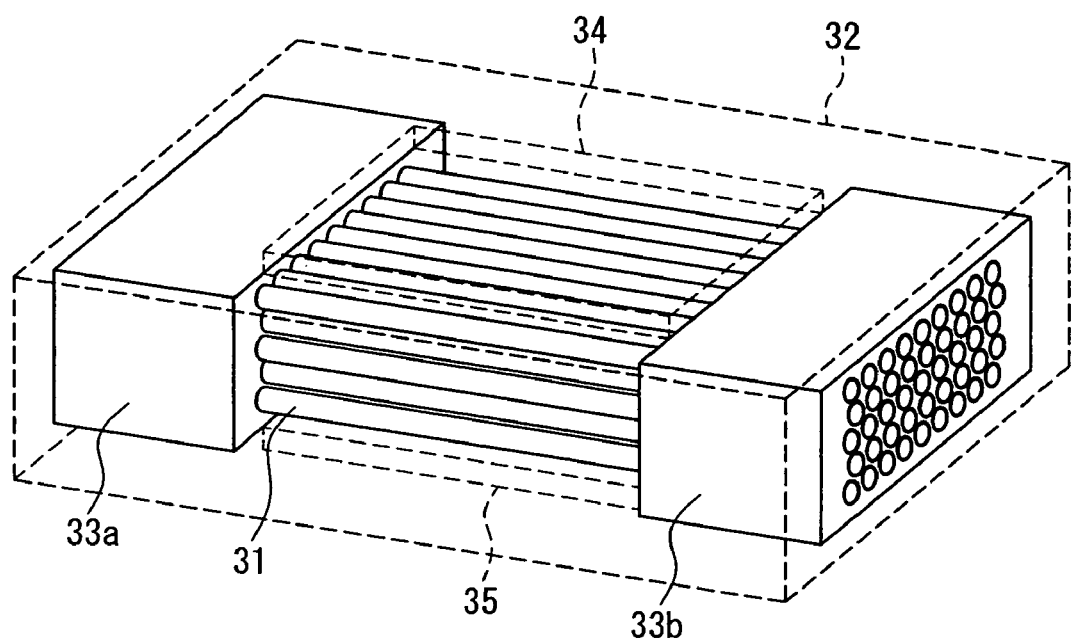
FIG. 11 is a perspective view illustrating tubes and sealing members composing the conventional multi-tubular heat exchanger shown in FIG. 10.

Next, an example in which blood flows through the tubes 1 while cold/hot water flows through the flow path 8 like the conventional heat exchanger shown in FIGS. 10A, 10B, and 11 is considered. In this example also, since the cold/hot water has a higher pressure, the cold/hot water outflows when the first, second, and third sealing members 3a, 3b, and 3c become leaky. In this example, the cold/hot water flows toward mouths of the tubes 1 on the blood inlet side and the artificial lung connected to the outlet side of the tubes 1. However, in this case also, the cold/hot water having leaked through the third sealing member 3c is retained in the gaps 7 temporarily, and is discharged through the second outlets 6 to outside the heat exchanger. Thus, in this example also, the sealing leakage can be detected, and the occurrence of blood contamination as described in the "background art" section can be suppressed.

As described above, if the heat exchanger shown in FIGS. 1A to 1C is applied in the heart-lung machine, outflow of cold/hot water due to sealing leakage can be detected. Further, as compared with the conventional heat exchanger shown in FIGS. 10A, 10B, and 11, the possibility of blood contamination can be decreased to a significantly low level.

The following describes an example of a method for manufacturing a heat exchanger according to the present invention while referring to FIGS. 3 to 8. It should be noted that the heat exchanger obtained by the following manufacturing method is identical to the heat exchanger shown in FIGS. 1A to 1C and 2, and includes a plurality of tubes 1 through which a first fluid passes, a tubular housing 2, and sealing members 3a to 3c. On sidewalls of the housing 2, an inlet 4 for introducing a second fluid into the housing, and a first outlet 5 for discharging the second fluid therefrom are formed. Still further, the sealing members are composed of three sealing members 3a to 3c that are formed with gaps 7 being provided therebetween. Still further, on sidewalls of the housing 2, second outlets 6 continuous with the gaps 7 are formed also.

Figure 3A:
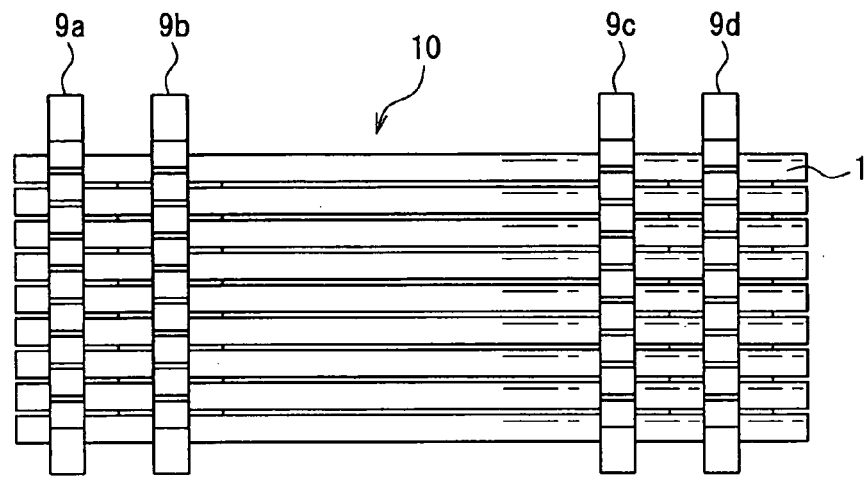
FIGS. 3A to 3C show a group of tubes composing a heat exchange module.
Figure 3B:
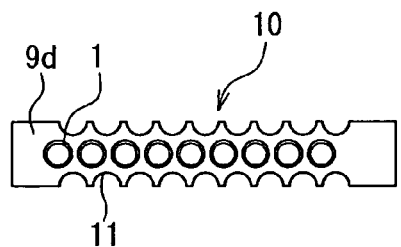
Figure 3C:
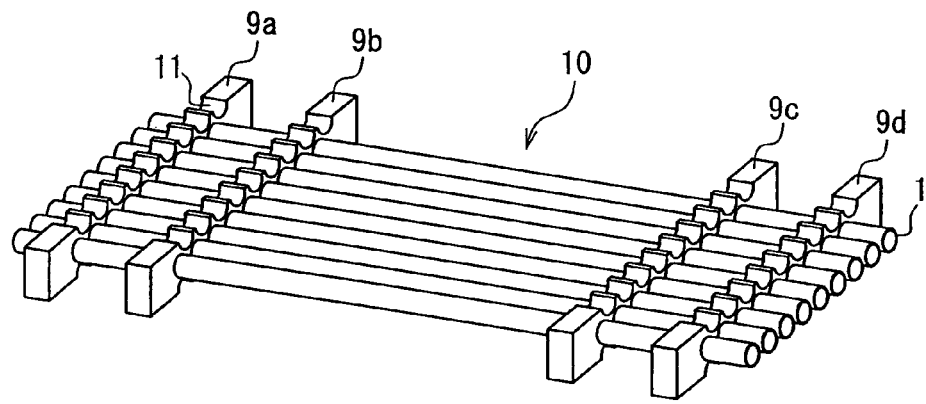
Figure 4A:
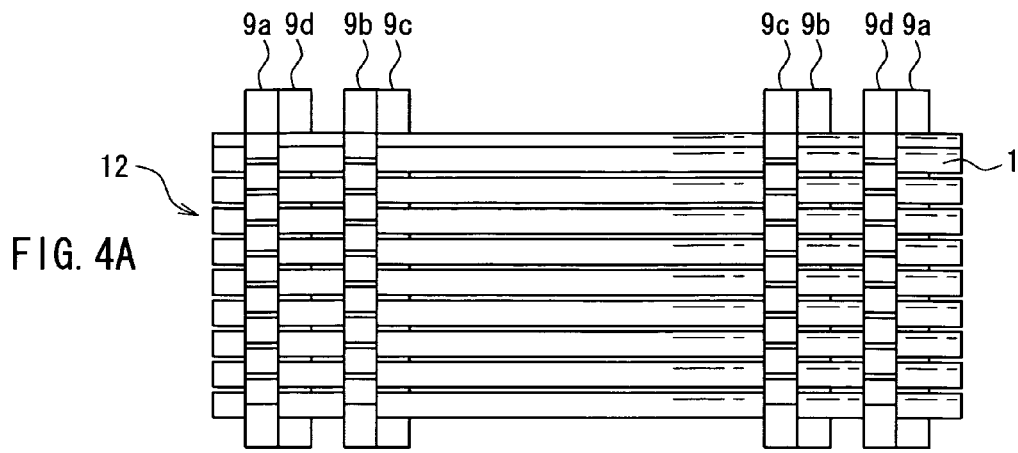
FIGS. 4A to 4C show the heat exchange module.
Figure 4B:
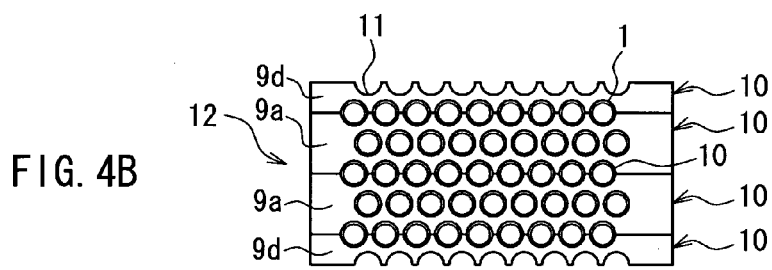
Figure 4C:
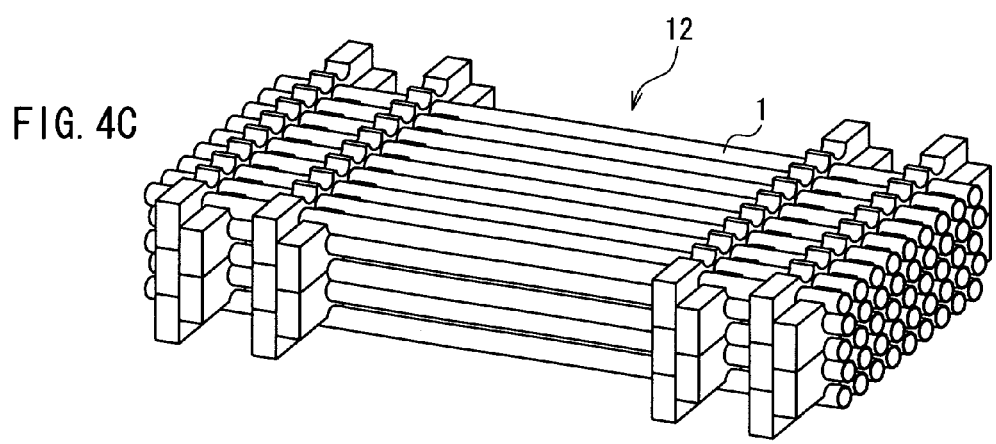
Figure 5:
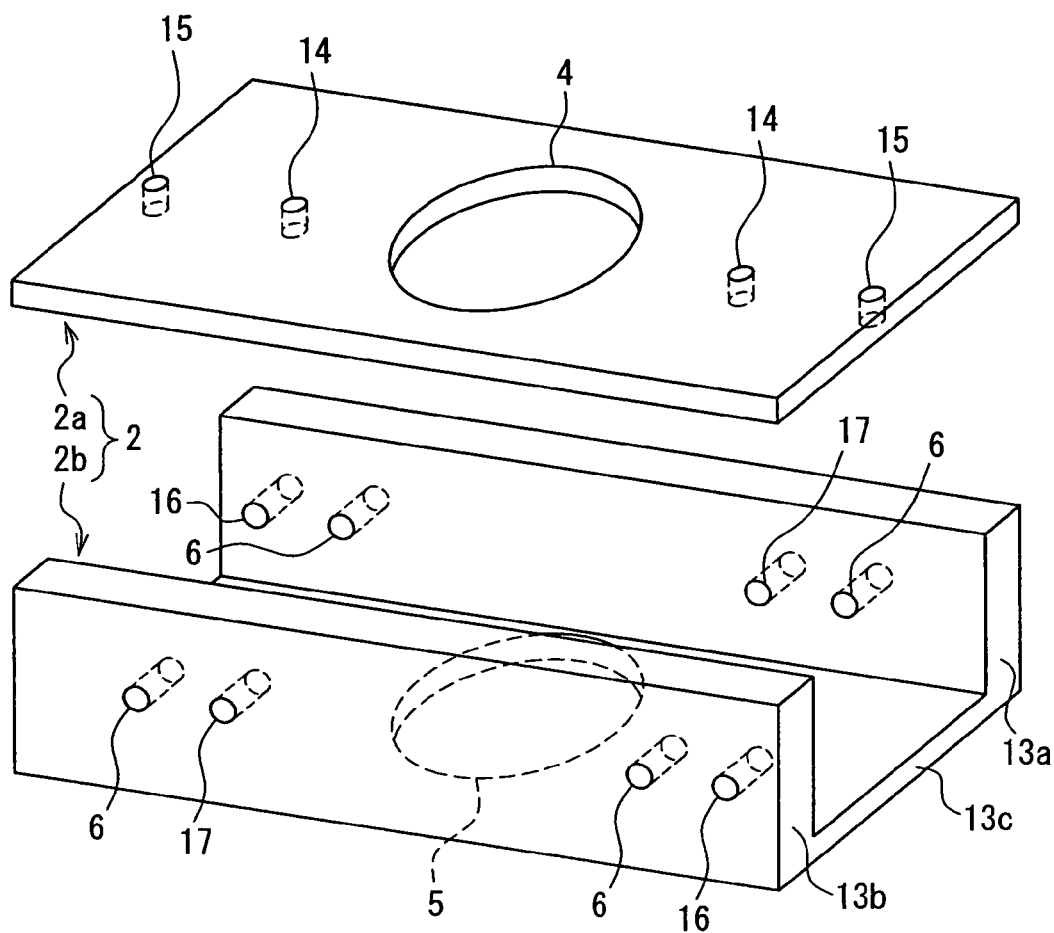
FIG. 5 is an exploded perspective view of a housing.
Figure 6A:
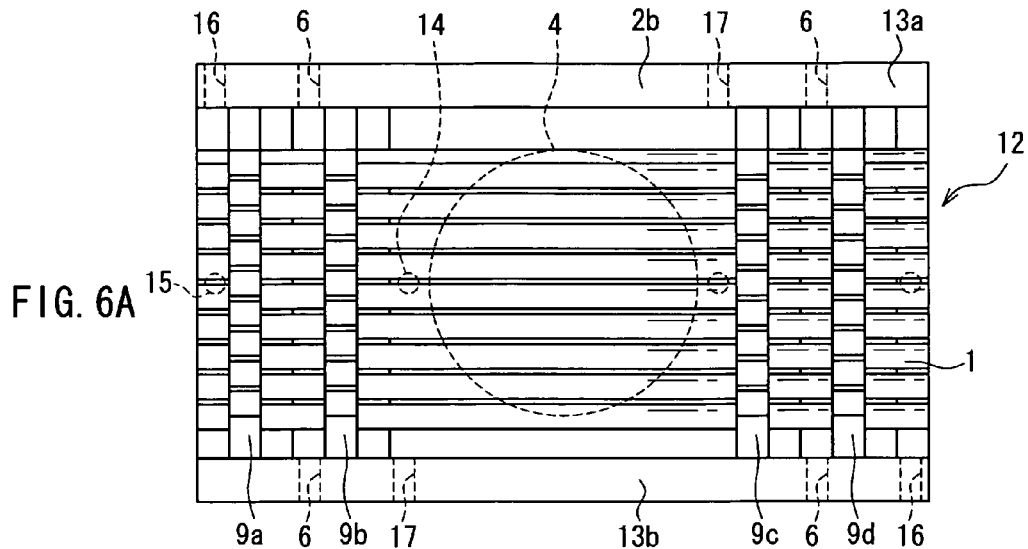
FIGS. 6A to 6C show the housing shown in FIG. 5 in which the heat exchange module shown in FIGS. 4A to 4C is disposed.
Figure 6B:
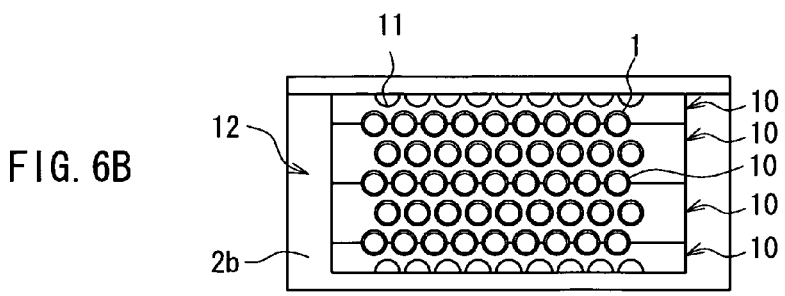
Figure 6C:
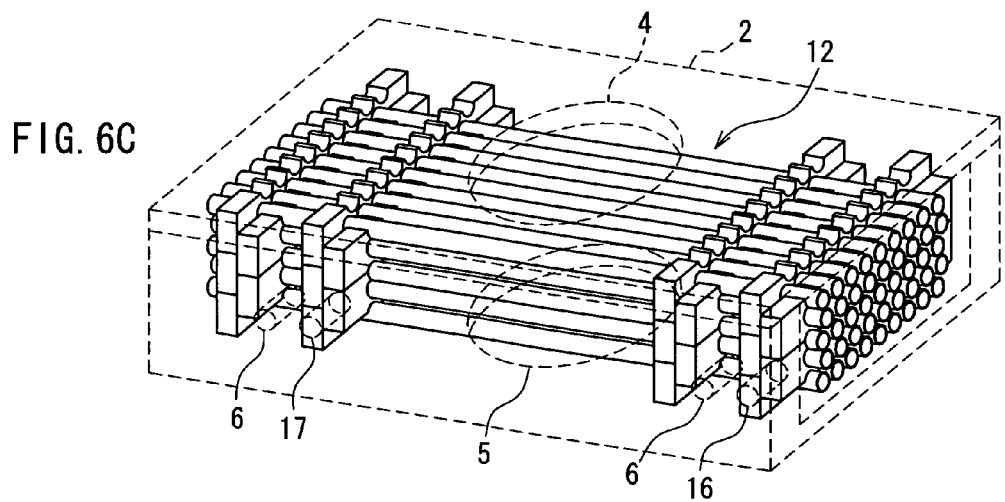
Figure 7:
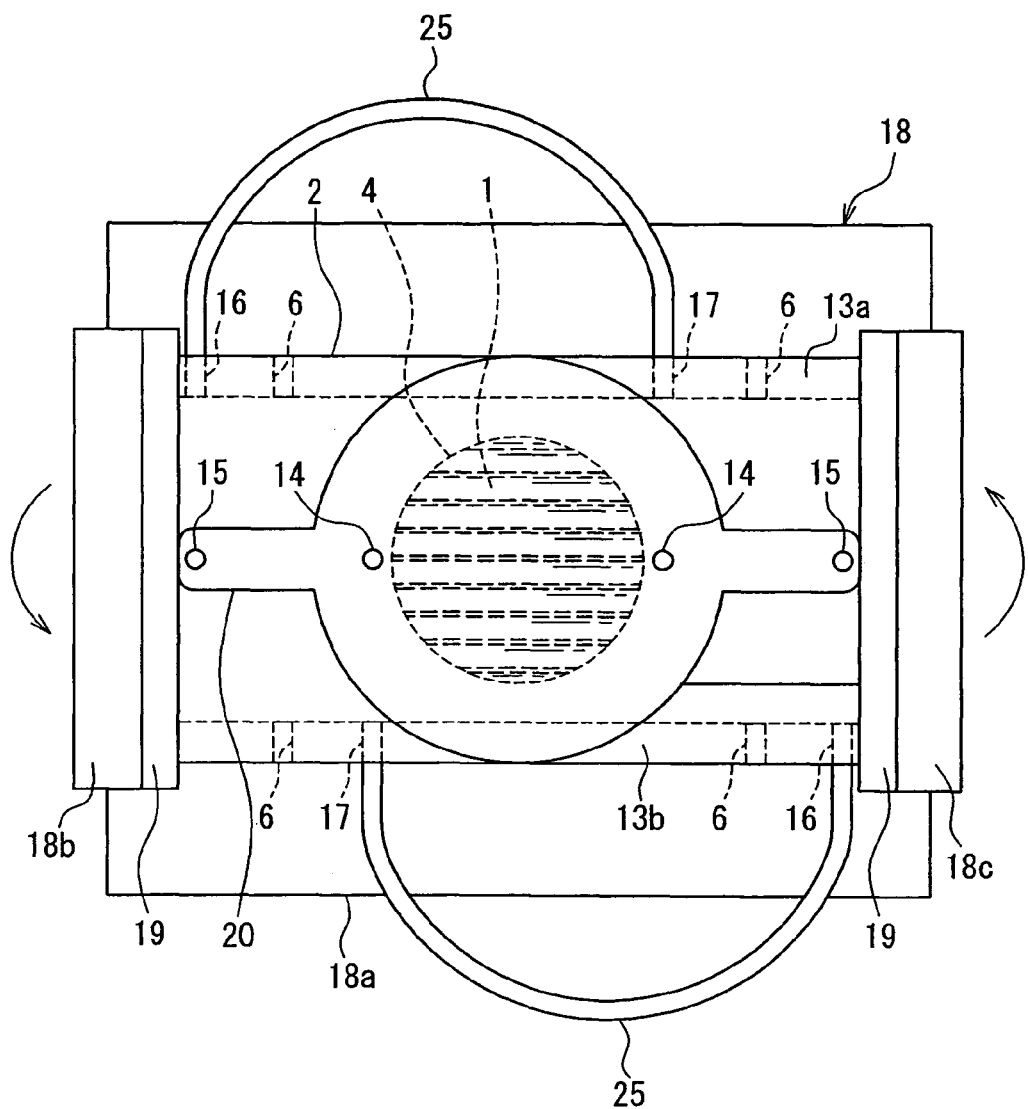
FIG. 7 is a top view illustrating the housing attached to a jig so that sealing members are formed.
Figure 8:
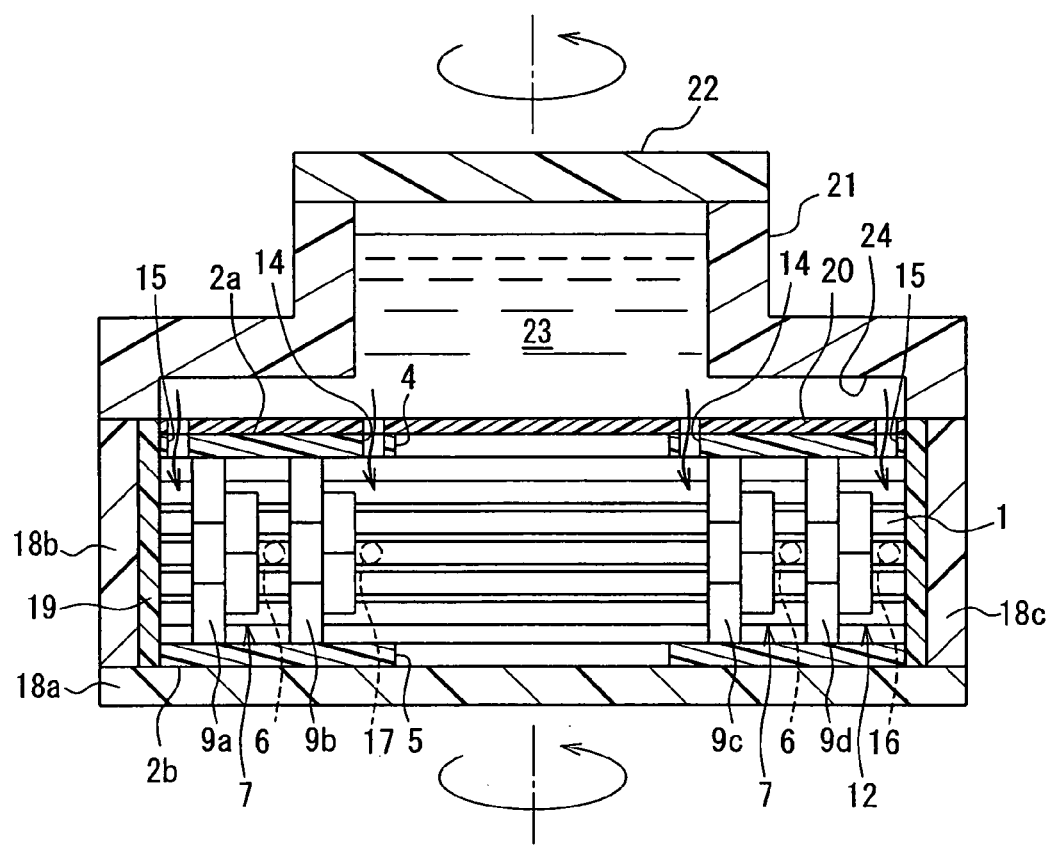
FIG. 8 is a cross-sectional view illustrating a step of forming the sealing members.

FIGS. 3A to 3C show a group of tubes composing a heat exchange module. FIG. 3A is a top view thereof, FIG. 3B is a front view thereof, and FIG. 3C is a perspective view thereof. FIGS. 4A to 4C show the heat exchange module. FIG. 4A is a top view thereof, FIG. 4B is a front view thereof, and FIG. 4C is a perspective view thereof. FIG. 5 is an exploded perspective view of a housing. FIGS. 6A to 6C show the housing shown in FIG. 5 in which the heat exchange module shown in FIGS. 4A to 4C is disposed. FIG. 6A is a top view thereof, FIG. 6B is a front view thereof, and FIG. 6C is a perspective view thereof. FIG. 7 is a top view illustrating the housing attached to a jig so that sealing members are formed. FIG. 8 is a cross-sectional view illustrating a step of forming the sealing members.

First, as shown in FIGS. 3A to 3C, a plurality of tubes 1 are arranged in parallel at intervals so that central axes of the tubes 1 are positioned on the same plane. Further, the tubes 1 are fixed and integrated in the arrayed state described above with use of band-like fixing members 9a to 9d extended in a direction perpendicular to the tube 1 central axis direction so as to encircle all the tubes. As a result, the tube group 10 is obtained.

In the example shown in FIGS. 3A to 3C, the formation of the tube group 10 is performed by insert molding that utilizes an upper die and a lower die (not shown). More specifically, in each of the upper die and the lower die, a plurality of first grooves (not shown) and a plurality of second grooves (not shown) are formed.

The first grooves in the upper die and the lower die are formed so that the tubes 1 can be disposed therein. Further, the first grooves in the upper die and the first grooves in the lower die are matched to each other when the upper and lower dies are joined. Therefore, by disposing the tubes 1 in the first grooves in either one of the upper and lower dies, the positioning of the tubes 1 is achieved.

The second grooves are formed so as to cross the first grooves orthogonally. Further, the second grooves in the upper die and the second grooves in the lower die are matched to each other when the upper and lower dies are joined, and form cavities that are used for forming the fixing members 9a to 9d.

Therefore, in the example of FIGS. 3A to 3C, the arrangement of the tubes 1 is achieved by, in either one of the upper and lower dies, disposing the tubes 1 in the plurality of first grooves formed in the die, respectively. By joining the upper and lower dies and injecting a resin material for forming the fixing members 9a to 9b into spaces formed by the second grooves in the upper and lower dies, the fixing members 9a to 9d are formed by injection molding. Through this injection molding, the tubes 1 are fixed with each other in an arranged state and integrated, as shown in FIGS. 3A to 3C.

It should be noted that examples of the resin material used for forming the fixing members include resins for injection molding that exhibit excellent fluidity and small shrinkage after molding, such as polycarbonate resins, polyamide resins, polyurethane resins, polypropylene resins, and poly(vinyl chloride) resins. Among these, a polycarbonate resin or a vinyl chloride resin is used preferably. This is because, as will be described later (see FIGS. 4A to 4C), in the present example, the fixing members 9a to 9d of the tube groups 10 neighboring to each other in the vertical direction are placed in dose contact with one another in the process of forming a heat exchange module, and a polycarbonate resin or a vinyl chloride resin facilitates achieving the dose contact property.

In the example shown in FIGS. 3A to 3C, the fixing members are four in total, which are the fixing members 9a to 9d (inner fixing members 9b and 9c, and outer fixing members 9a and 9d disposed relatively outward with respect to the inner fixing members 9b and 9c, respectively). They are disposed at intervals along the tube 1 central axis direction. As seen in FIG. 3B, a plurality of recessed portions 11 are formed in the fixing members 9a to 9d so as to facilitate the formation of a heat exchange module, which will be described later. As shown in FIGS. 3A to 3C, a plurality of the tube groups 10 are to be formed.

Further, in the example shown in FIGS. 3A to 3C, the inner fixing members 9b and 9c are arranged so that when the heat exchange module to be described later is disposed in a housing, the inlet 4 and the first outlet 5 (see FIGS. 1A to 1C and 2) are positioned in the space between the fixing members 9b and 9c. In other words, in the example shown in FIGS. 3A to 3C, the interval between the fixing members 9b and 9c is set to be greater than the diameter of the inlet 4 as well as than the diameter of the first outlet so that the inlet 4 and the first outlet 5 are positioned between the fixing members 9b and 9c.

Still further, a space between the outer fixing member 9a and the inner fixing member 9b and a space between the outer fixing member 9d and the inner fixing member 9c form the gaps 7, which are the gap 7 between the third sealing member 3c and the first sealing member 3a and the gap 7 between the third sealing member 3c and the second sealing member 3b (see FIGS. 1A to 1C and 2). Therefore, the interval between the fixing members 9a and 9b and the interval between the fixing members 9c and 9d preferably are set in ranges such that the gaps 7 to be formed are allowed to exhibit the above-described function and that the heat exchanger is not made bulky.

Next, as shown in FIGS. 4A to 4C, the heat exchange module 12 is formed by stacking a plurality of the tube groups 10 as shown in FIGS. 4A to 4C. Here, the stacking of the plurality of tube groups 10 is performed in a manner such that the fixing members 9a to 9d of each tube group 10 are brought into close contact, in the tube 1 central axis direction, with the fixing members 9a to 9d of another tube groups 10 immediately above and below the foregoing group 10.

More specifically, in the example shown in FIGS. 4A to 4C, the stacking of the plurality of tube groups 10 is performed so that the fixing member 9a of each of the tube groups 10 is brought into dose contact with the fixing member 9d of another tube groups 10 immediately above and below the foregoing group, and likewise, the fixing members 9b, 9c, and 9d of each tube group 10 are brought into dose contact with the fixing members 9c, 9b, and 9a of another tube groups 10 immediately above and below the foregoing group, respectively. By so doing, in the heat exchange module 12 shown in FIGS. 4A to 4C, ends of the tubes 1 in the tube groups 10 are aligned, and side faces of the fixing members 9a to 9d of the tube groups 10 fall in the same planes. It should be noted that it is intended by bringing the fixing members 9a to 9d of the vertically neighboring tube groups 10 into close contact with one another: namely, in a sealing member forming process (see FIGS. 7 and 8) by filling a resin material, which will be described later, the resin material is to be prevented from flowing into the gaps 7.

Further, in the example of FIGS. 4A to 4C, the stacking of the plurality of tube groups 10 is performed in a manner such that the tubes 1 composing each tube group 10 are fit in the recessed portions 11 provided in the fixing members 9a to 9d of other tube groups 10 immediately above and below the foregoing group 10. As a result, as shown in FIGS. 1A to 1C and 2, in a cross-sectional plane perpendicular to the tube 1 central axis direction, a figure bounded by lines meeting at the cross-sectional center of each of the tubes 1 in each tube group and the cross-sectional centers of two tubes most adjacent to the foregoing tube 1 in another tube group immediately above or below the foregoing tube group is an equilateral triangle.

Next, the heat exchange module 12 shown in FIGS. 4A to 4C is housed in the housing 2 shown in FIG. 5. In the example shown in FIG. 5, the housing 2 is composed of a lid 2a and a main body 2b. In a central portion of the lid 2a, the inlet 4 is provided. The main body 2b is composed of side plates 13a and 13b opposed to each other, and a bottom plate 13c, and its cross section has a straight-sided U shape. In a central portion of the bottom plate 13c, the first outlet 5 is provided. The side plates 13a and 13b are provided with the second outlets 6.

Further, injection holes 14 and 15 are formed in the lid 2a, so that a material is injected therethrough upon the formation of the sealing members, which will be described later, and air vents 16 and 17 are formed in the side plates 13a and 13b of the main body 2b. The injection holes 14 and 15, the air vents 16 and 17, and the filling of a material with use of these are described later.

Further, as shown in FIGS. 6A to 6C, the installation of the heat exchange module 12 in the housing 2 is carried out in a manner such that the tube 1 central axis direction is oriented in a longitudinal axis direction of the housing 2. Further, in this step, exposed portions of the fixing members 9a to 9d in the tube groups 10 on surfaces of the heat exchange module 12 are brought into dose contact with or bonded with inner surfaces of the housing 2. It should be noted that FIG. 6A indicates the lid 2a with dotted lines for the purpose of illustration. Further, FIG. 6C indicates the housing 2 entirely with dotted lines.

In the example of FIGS. 6A to 6C, the exposed portions of the fixing members 9a to 9d in the tube groups 10 on surfaces of the heat exchange module 12 are bonded with the inner surfaces of the housing 2 (inner surfaces of the lid 2a and the main body 2b). An adhesive used herein is, for instance, a urethane-based adhesive or an epoxy-based adhesive.

It should be noted that in the present embodiment, it is not necessary to bring all the exposed portions of the fixing members 9a to 9d on surfaces of the heat exchange module 12 into close contact with the inner surfaces of the housing, or to bond the same thereto. This step of bringing the exposed portions on the surfaces into dose contact with the inner surfaces of the housing 2 or bonding the same thereto may be carried out to an extent such that in the later-described step of forming the sealing members by filling a resin material (see FIGS. 7 and 8), the resin material should not flow into the gaps 7.

Next, as shown in FIGS. 7 and 8, the sealing members 3a to 3c (see FIGS. 1A to 1C and 2) are formed in the housing 2 in which the heat exchange module 12 is installed, by filling a resin material. More specifically, as shown in FIG. 7, first the housing in which the heat exchange module 12 is installed is attached to a jig 18.

The jig 18 is composed of a main body plate 18a, and a pair of pressure plates 18b and 18c that sandwich the housing 2 so as to stop up the opposed openings of the housing 2. Packings 19 are provided between the pressure plate 18b and the housing 2 and between the pressure plate 18b and the housing 2. With this configuration, the resin material is prevented from leaking out via the openings of the housing 2, as well as is prevented from intruding in the tubes 1. It should be noted that 25 denotes a tube, which will be described later.

Further, the jig 18 is configured to be rotational around an axis extending from the center of the inlet 4 to the center of the first outlet 5. As described later, the filing of the resin material is carried out while the jig 18 is rotated. Further, on an upper face of the housing 2, a mask 20 is applied over a top face of the housing 2 to prevent the intrusion of the resin material through the inlet 4. However, holes are provided in the mask 20 so that the injection holes 14 and 15 are not stopped up.

Next, as shown in FIG. 8, an injection pot 21 is attached on the top face of the housing 2. The injection pot 21 includes a flow path 24 for guiding a resin material 23 filled in the injection pot 21 to the injection holes 14 and 15. Here, 22 denotes a lid of the injection pot. It should be noted that in FIG. 8, the heat exchange module 12 is shown as viewed from a side thereof.

Further, as seen from FIG. 8, the injection hole 15 shown in the left-side part of the drawing is formed so as to be connected to interstices around the tubes 1 between the opening of the housing on the left side as viewed in the drawing and the outer fixing member (9a or 9d) of each tube group 10 on the left side as viewed in the drawing (hereinafter referred to as "first housing space"). On the other hand, the injection hole 15 shown in the right-side part of the drawing is formed so as to be connected to interstices around the tubes 1 between the opening of the housing on the right side as viewed in the drawing and the fixing member (9d or 9a) of each outer tube group 10 on the right side as viewed in the drawing (hereinafter referred to as "second housing space"). Further, the injection holes 14 are formed so as to be connected with a space (hereinafter referred to as "third housing space") positioned between the two inner fixing members 9b and 9c of each tube group 10 in the housing 2.

Therefore, when the resin material 23 is filled into the injection pot 21, the resin material 23 intrudes into the inside of the housing through the injection holes 14 and 15. Here, as described above, the portions of the fixing members 9a to 9d of each tube group 10 that are exposed on surfaces of the heat exchange module 12 are bonded to inner surfaces of the housing 2. Therefore, the resin material is filled in only the first, second, and third housing spaces, whereby the gaps 7 are formed.

Further, in the example shown in FIG. 8, the filling of the resin material is carried out by rotating the jig 18 as described above, which causes the housing 2 and the injection pot 21 to rotate also. Therefore, centrifugal force developed by the foregoing rotation is applied to the resin material filled in the housing 2. As a result, a flow path 8 in a columnar shape as shown in FIG. 2 is formed with the resin material filled in the third housing space.

It should be noted that the first and second housing spaces are completely closed spaces when the injection of the resin material through the injection holes 15 is started. Therefore, without an escape through which air goes out, the injection of the resin material over a certain extent is inhibited. To cope with this, as shown in FIG. 7, the air vent 16 connected to the first housing space and the air vent 17 connected to the third housing space are provided in the side plate 13a of the housing (see FIG. 5). Further, the air vent 16 connected to the second housing space and the air vent 17 connected to the third housing space are provided in the side plate 13b of the housing (see FIG. 5). Still further, the air vents 16 and 17 in each side plate are connected with each other via a tube 25.

The injection of the resin material with use of the injection pot 21 shown in FIG. 8 is carried out until the first and second housing spaces are filled with the resin material and the flow path 8 (see FIGS. 1A to 1C and 2) matched with the inlet 4 and the first outlet 5 is formed in the third housing space. The rotation of the jig 18 is stopped when the fluidity of the resin material thus filled decreases and the shape of the flow path 8 is maintained.

As a result, as shown in FIGS. 1A to 1C and 2, the first sealing member 3a is formed in the first housing space, while the second sealing member 3b is formed in the second housing space. Besides, the third sealing member 3c is formed in the third housing space, whereby the flow path 8 is formed also. Further, in the present embodiment, the three sealing members 3a and 3c are formed through one step of the filling of resin material.

Examples of the resin material used for forming the sealing members 3a to 3c in the present embodiment include thermosetting resins such as silicon resins, polyurethane resins, and epoxy resins. Among these, a polyurethane resin or an epoxy resin is preferred since it has excellent adhesivity to a material used for forming the tubes 1 (for instance, a metal material) and a material used for forming housing 2 (for instance, a resin material such as a polycarbonate resin).

Still further, in the case where the tubes 1 are formed with a metal material and the housing 2 is formed with a resin material, the sealing members 3a to 3c preferably are formed to have a two-layer structure by injecting resin materials of different types successively. For instance, a polyurethane resin and an epoxy resin can be used. In such an embodiment, the dose contact property, the adhesivity, and the compatibility can be improved between the sealing members 3a to 3c and the tubes 1, as well as between the sealing members 3a to 3c and the housing.

It should be noted that in the example shown in FIG. 8, a polyurethane resin is used as a resin material. Further, the injection of a polyurethane resin is carried out by setting the rotation rate of the jig 18 to 1500 rpm to 3000 rpm, the amount to be injected to 20 ml to 100 ml, the inner temperature of the injection pot 21 to room temperature (25° C.) to 60° C., and the time of rotation of the jig 18 to 30 min to 360 min.

By using the heat exchanger manufacturing method of the present invention as described above, the plurality of tubes 1 can be arranged simply, easily, and regularly at uniform pitches, and this process can be carried out within a short time. Therefore, by the heat exchanger manufacturing method of the present invention, a multi-tubular heat exchanger can be provided at a lower production cost. Accordingly, it is possible to make a contribution to the cost reduction of an apparatus in which the obtained heat exchanger is used, for instance, in the cost reduction of a heart-lung machine.

The heat exchanger manufacturing method of the present invention can be used for manufacturing a heat exchanger other than that shown in FIGS. 1A to 1C and 2, for instance, for manufacturing a heat exchanger shown in FIGS. 10A, 10B, and 11. In this case, only two fixing members may be disposed in the manufacture of the tube group 10 shown in FIGS. 3A to 3C. Further, the resin material for forming the sealing members may be filled only in interstices around the tubes between the openings of the housing and the fixing members. Still further, a resin material may be filled so that a flow path that guides the second fluid introduced through the inlet toward the outlet is formed in a space between the two fixing members of each tube group in the housing.

Figure 9:
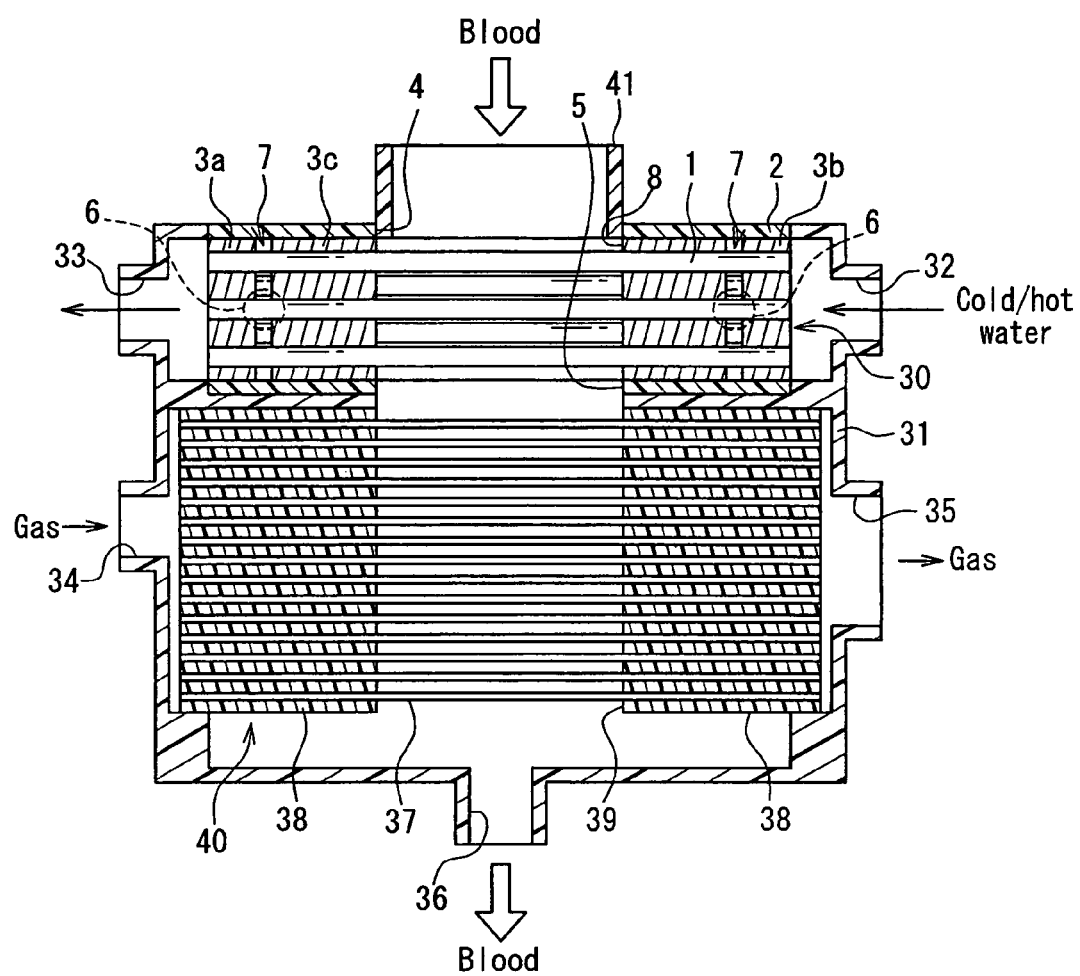
FIG. 9 is a cross-sectional view illustrating a configuration of an example of a heart-lung machine according to the present invention.

Next, a heart-lung machine in which the heat exchanger of the present invention is used is described with reference to FIG. 9. FIG. 9 is a cross-sectional view illustrating a configuration of an example of a heart-lung machine according to the present invention. It should be noted that among the reference numerals shown in FIG. 9, the same numerals as those shown in FIGS. 1A to 1C and 2 designate the same members as those shown in FIGS. 1A to 1C and 2.

As shown in FIG. 9, a heart-lung machine includes a heat exchanger 30 and an artificial lung 40, which are installed in a housing 31. The housing 31 includes a cold/hot water introduction path 32 through which cold/hot water for heat exchange is introduced, a cold/hot water discharge path 33 through which the cold/hot water is discharged, a gas introduction path 34 through which oxygen gas is introduced, and a gas discharge path 35 through which carbon dioxide and the like removed from blood is discharged.

The heat exchanger 30 has the same configuration as that shown in FIGS. 1A to 1C and 2. In the heat exchanger 30, cold/hot water flows through the tubes 1, blood of a patient flows through the flow path 8. It should be noted that a pipe 41 for guiding blood is connected to the inlet 4 provided in the housing 2 of the heat exchanger 30.

The artificial lung 40 includes a plurality of hollow fiber films 37 and a pair of sealing members 38. The pair of sealing members 38 seal both ends of the plurality of hollow fiber films 37 so that blood does not intrude into the gas introduction path 34 and the gas discharge path 35. The sealing with use of the sealing members 38 is carried out so that both the ends of the hollow fiber films 37 are exposed. With this configuration, the gas introduction path 34 and the gas discharge path 35 are connected with each other via the hollow fiber films 37.

Further, a space in the artificial lung 40 in which the sealing members 38 are not present forms a blood flow path 39, in which the hollow fiber films 37 are exposed. Still further, a blood inlet side of the blood flow path 39 is connected to an outlet side of the flow path 8 of the heat exchanger 30.

Accordingly, the blood subjected to heat exchange while running through the flow path 8 flows into the blood flow path 39, where the blood is brought into contact with the hollow fiber films 37. Here, oxygen gas running through the hollow fiber film 37 is taken into the blood. The blood having captured oxygen gas is discharged to the outside via a blood discharging outlet 36 provided in the housing 31, and then returned to the patient. On the other hand, carbon dioxide in the blood is taken into the hollow fiber films 37 and thereafter discharged through the gas discharge path 35.

Thus, in the heart-lung machine shown in FIG. 9, the temperature adjustment of blood is carried out by the heat exchanger 30, and blood thus subjected to temperature adjustment is subjected to gas exchange by the artificial lung 40. Here, even if the sealing is leaky in the heat exchanger 30 and cold/hot water running through the tubes 1 leaks out, the leaked cold/hot water is retained in the gaps 7, and thereafter discharged to the outside through the second outlets 6 of the heat exchanger 30. Therefore, the sealing leakage can be detected, and contamination of blood with the cold/hot water can be prevented.

INDUSTRIAL APPLICABILITY

With the present invention, it is possible to provide a heat exchanger and a heart-lung machine capable of preventing a fluid running through the inside of tubes or a fluid running over surfaces of tubes from being contaminated due to sealing leakage, and to provide a method for manufacturing a heat exchanger with which the production cost can be reduced. The heat exchanger of the present invention can be used as a heat exchanger for medical use, which could possibly cause loss of life if sealing leakage occurs.

The invention claimed is:

1. A heat exchanger comprising at least a plurality of tubes through which a first fluid passes, a housing in which the tubes are installed, and sealing members for sealing a second fluid that flows over surfaces of the tubes, wherein the housing includes an inlet for introducing the second fluid into the housing, as well as a first outlet and second outlets for discharging the second fluid out of the housing, the tubes are arranged in parallel with one another in the housing, the sealing members include at least a first sealing member positioned on one of end sides of the tubes, a second sealing member positioned on the other end side of the tubes, and a third sealing member positioned between the first and second sealing members, the third sealing member is provided so that a gap is provided between the first sealing member and the third sealing member while another gap is provided between the second sealing member and the third sealing member, and that a flow path is formed in the third sealing member for guiding the second fluid introduced through the inlet toward the first outlet, and the second outlets are provided in the housing so as to be connected to the gaps, respectively, the inlet and the first outlet are formed in a round shape, the flow path for the second fluid is formed in a columnar shape with an axis direction thereof extending from the center of the inlet to the center of the first outlet, so as to cross over outer surfaces of the tubes laterally, and mouths of the flow path for the second fluid are matched with the inlet and the first outlet, respectively.

2. The heat exchanger according to claim 1, wherein the tubes are arranged so that in a cross-sectional plane perpendicular to a direction of central axes of the tubes, a figure bounded by lines meeting at cross-sectional centers of three neighboring tubes is an equilateral triangle.

3. The heat exchanger according to claim 1, wherein the second fluid passing through the flow path is blood, and the heat exchanger is adapted to form a part of a heart-lung machine.

4. A heart-lung machine comprising the heat exchanger according to claim 1.

* * * * *